(12) United States Patent
Sekine et al.

(10) Patent No.: US 10,704,020 B2
(45) Date of Patent: Jul. 7, 2020

(54) INCUBATOR

(71) Applicant: PHC HOLDINGS CORPORATION, Tokyo (JP)

(72) Inventors: Hironobu Sekine, Gunma (JP); Koichi Kobayashi, Tochigi (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 3 days.

(21) Appl. No.: 16/352,329

(22) Filed: Mar. 13, 2019

(65) Prior Publication Data

US 2019/0211301 A1 Jul. 11, 2019

Related U.S. Application Data

(63) Continuation of application No. 15/719,323, filed on Sep. 28, 2017, now abandoned, which is a (Continued)

(30) Foreign Application Priority Data

Mar. 30, 2015 (JP) .................................. 2015-069862

(51) Int. Cl.
*C12M 1/36* (2006.01)
*C12M 1/00* (2006.01)
(Continued)

(52) U.S. Cl.
CPC ............ *C12M 41/14* (2013.01); *C12M 23/04* (2013.01); *C12M 41/34* (2013.01); *C12M 41/48* (2013.01)

(58) Field of Classification Search
CPC ...... C12M 41/14; C12M 41/34; C12M 41/48; C12M 23/04
(Continued)

(56) References Cited

U.S. PATENT DOCUMENTS

| 5,519,188 A | 5/1996 | Yuichi et al. |
| 5,773,287 A | 6/1998 | Binder |

FOREIGN PATENT DOCUMENTS

| EP | 2 031 051 A1 | 3/2009 |
| EP | 2 573 163 A1 | 3/2013 |
| JP | H05-227942 A | 9/1993 |

OTHER PUBLICATIONS

Search Report issued in corresponding International Patent Application No. PCT/JP2016/057908, dated Apr. 5, 2016, with English translation.
(Continued)

*Primary Examiner* — Liban M Hassan
(74) *Attorney, Agent, or Firm* — McDermott Will & Emery LLP (57) ABSTRACT

An incubator includes: an insulated box including an incubation space surrounded by multiple inner faces; a humidifying unit that humidifies an incubation space; a first heating unit that heats a first inner face among the multiple inner faces, with electric power supplied; a second heating unit that heats a second inner face, different from the first inner face, with electric power supplied; and a control unit that controls the magnitude of electric power supplied to each of the first heating unit and the second heating unit. The control unit repeatedly changes the magnitude of electric power supplied to the first heating unit at first timing, and also repeatedly changes the magnitude of electric power supplied to the second heating unit at second timing different from the first timing.

5 Claims, 6 Drawing Sheets

Related U.S. Application Data continuation of application No. PCT/JP2016/057908, filed on Mar. 14, 2016.

(51) Int. Cl.
*C12M 1/34* (2006.01)
*C12M 1/12* (2006.01)

(58) Field of Classification Search
USPC .......................................... 435/286.1, 303.1
See application file for complete search history.

(56) References Cited

OTHER PUBLICATIONS

Extended European Search Report issued in corresponding EP Patent Application No. 16772220.6, dated Jan. 31, 2018.
Non-Final Office Action issued in U.S. Appl. No. 15/719,323, dated Dec. 14, 2018.

INCUBATOR

This application is a continuation of U.S. patent application Ser. No. 15/719,323, filed on Sep. 28, 2017, which is a continuation of International Patent Application No. PCT/JP2016/057908, filed on Mar. 14, 2016, which is based upon and claims the benefit of priority from the prior Japanese Patent Application No. 2015-069862, filed on Mar. 30, 2015, the entire content of each is incorporated herein by reference.

BACKGROUND OF THE INVENTION

1. Field of the Invention

The present disclosure relates to an incubator.

2. Description of the Related Art

Conventionally, incubators for cultivation of cells and microorganisms and so on, in incubation chambers have been known. Such an incubator comprises a heater for heating the inside of the incubation chamber where a humidification pan is placed, and, by controlling the heater, the inside of the incubation chamber may be maintained at a predetermined temperature (37 degrees C., for example) and also at predetermined humidity (95% RH, for example) based on the predetermined temperature, for example.

Also, there has been disclosed, for example, an incubator that includes a heating element for heating water stored in a recess formed on the bottom face, a heating element for heating the inside of the incubation chamber except for the recess, and a heating element provided on an insulated door, which is openably and closably attached to the insulated box body, and, by controlling electric power supplied to the three heating elements so as to maintain the temperature of the water in the recess lower than the temperature in the incubation chamber, supersaturated content of water within the incubation chamber is returned to the recess, thereby preventing dew condensation (see Patent Document 1).

This incubator also comprises a temperature detection device for detecting a temperature within the incubation chamber and is configured to control each of the multiple heating elements based on the detection result of the temperature detection device.

PRIOR ART REFERENCE

Patent Document

[Patent Document 1] Japanese Unexamined Patent Application Publication No. 5-227942

SUMMARY OF THE INVENTION

However, temperatures within the incubation chamber are not necessarily uniform. Accordingly, even when the temperature near the temperature detection device stands at a desired value, the temperature of a partial region in the incubation chamber may be relatively lower than the temperature therearound. In this case, dew condensation may be caused on the wall surface in the region of which the temperature is relatively lower than the temperature therearound. The dew condensation may cause the problem of growth of unwanted bacteria in the condensed water, which negatively affects the cultures.

The present invention is made in view of such a situation, and a purpose thereof is to provide a new technique for preventing dew condensation in an incubator.

To solve the problem above, an incubator of an embodiment of the present invention includes: an insulated box including an incubation space surrounded by a plurality of inner faces; a humidifying unit that humidifies an incubation space; a plurality of heating units that respectively heat the plurality of inner faces, with electric power supplied; and a control unit that controls the magnitude of electric power supplied to each of the plurality of heating units. The control unit periodically and repeatedly changes the magnitude of electric power supplied to the plurality of heating units, at timing different for each of the plurality of inner faces.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

In the following, the present invention will be described based on suitable embodiments with reference to the drawings. Like reference characters designate like or corresponding elements, members and processes throughout the views. The description of them will not be repeated for brevity. Reference herein to details of the illustrated embodiments is not intended to limit the scope of the claims. It should be understood that not all of the features and the combination thereof discussed are essential to the invention.

First Embodiment (Schematic Configuration of Incubator)

Figure 1:
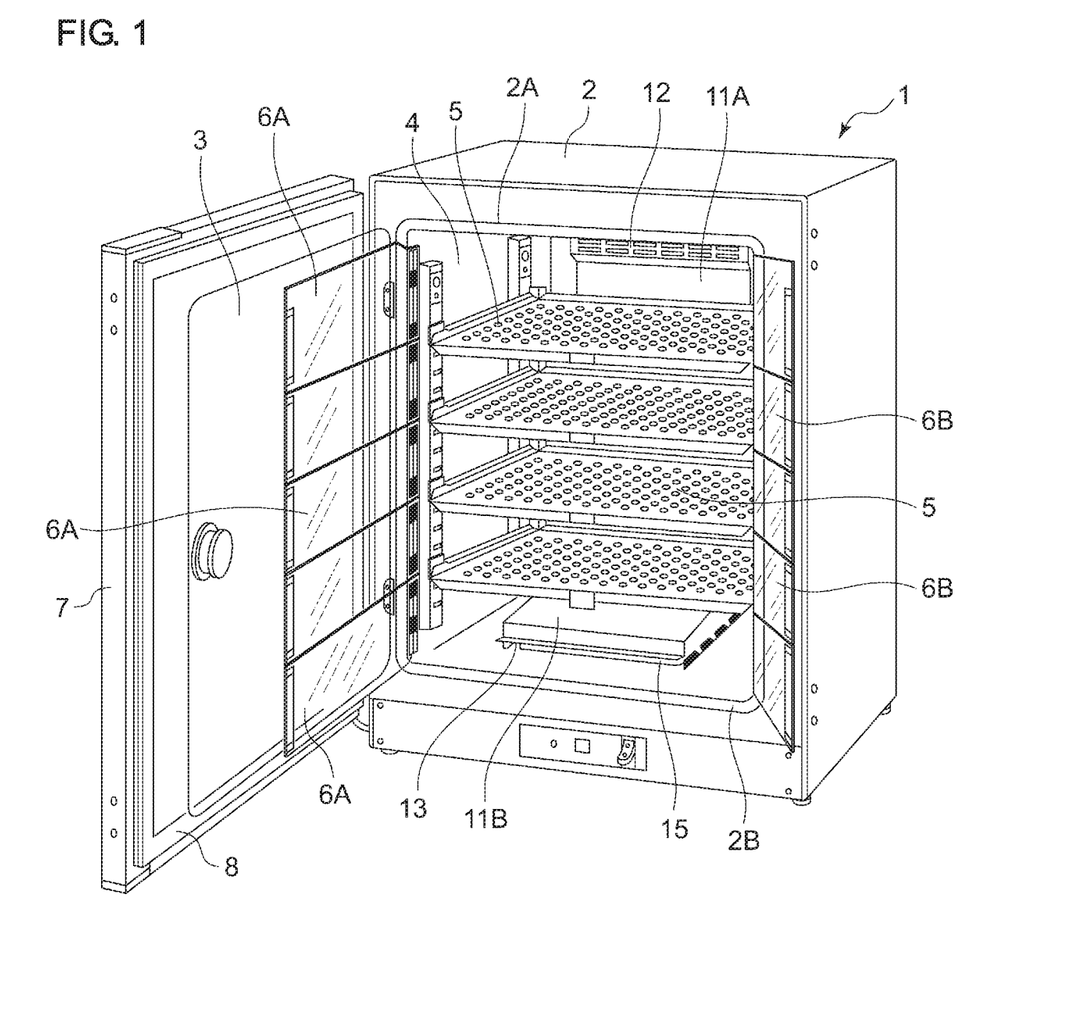
FIG. 1 is a perspective view that shows a schematic configuration of an incubator according to an embodiment.
Figure 2:
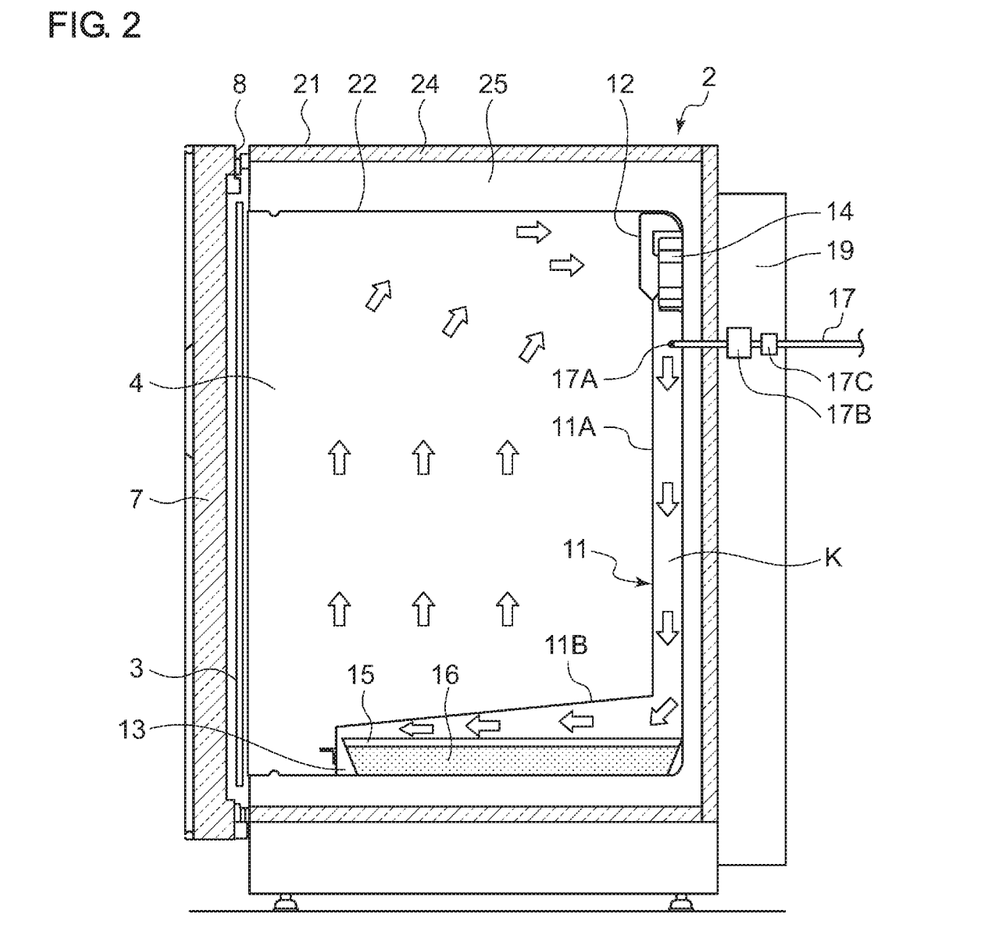
FIG. 2 is a sectional view of the incubator according to the embodiment.

FIG. 1 is a perspective view that shows a schematic configuration of an incubator according to an embodiment. FIG. 1 shows the state where an insulated door of the incubator is open. FIG. 2 is a sectional view of the incubator according to the embodiment.

As shown in FIGS. 1 and 2, an incubator 1 comprises a left opening door (more specifically, an outer door and an inner door) and small doors, which are hinged double doors. In the incubator 1, a space surrounded by an insulated box body 2, which includes an opening 2A on the front side, and a transparent door 3, which is an inner door openably and closably covering the opening 2A, is formed as an incubation chamber 4. The transparent door 3 is openably and closably hinged to the insulated box body 2 on the left side and hermetically covers the opening 2A with a gasket 2B provided as a seal member on the frontage of the incubation chamber 4.

The interior of the incubation chamber 4 is horizontally partitioned by multiple shelves 5 (partitioned into five by four shelves in this example). When the incubator 1 is used as a $CO_2$ incubator, for example, the $CO_2$ concentration is often set and maintained at about 5%, so that, after the door is closed, $CO_2$ gas is supplied into the incubation chamber 4 for $CO_2$ concentration control. Accordingly, multiple pairs of small doors 6A and 6B, which are hinged double doors, are provided for the respective sections (five pairs in this example) inside the transparent door 3 so that outside air is not introduced into the whole incubation chamber 4 partitioned into multiple sections even when the transparent door 3 is opened. An insulated door 7 is openably and closably hinged to the insulated box body 2 and functions as an outer door to prevent heat from entering through the opening 2A of the incubation chamber 4, and a gasket 8 containing a magnet is provided along the circumference on the back side of the insulated door 7.

On the back face and the bottom face of the incubation chamber 4 is provided a duct 11, which consists of a back duct 11A and a bottom duct 11B that each include a space for forming a gas passage K. In the incubation chamber 4, forced gas circulation is performed, in which gas within the incubation chamber 4 is suctioned through a suctioning port 12, formed above the back duct 11A, and then expelled through an expulsion port 13, provided on the right and left sides and the front side of the bottom duct 11B, into the incubation chamber 4. Within the duct 11 (an upper part in FIG. 2), a circulation blower 14 is provided for the forced gas circulation. The circulation blower 14 comprises a fan, a motor, and a shaft; the motor is disposed in a machine chamber 19 provided outside and on the back face of the incubation chamber 4, as described later, and the shaft extends from the motor in the machine chamber 19 to the gas passage K, piercing the back face of the insulated box body 2, to be connected to the fan.

Within the duct 11 and on the bottom face of the incubation chamber 4, a humidification pan 15 for storing water for humidification (i.e., humidifying water) 16 is placed and heated by a heater provided outside and on the bottom face of an inner box 22 made of metal, such as stainless steel, so that the water is evaporated. By disposing the humidification pan 15 within the duct 11 and on the bottom face of the incubation chamber 4, humidified gas can be efficiently expelled through the gas passage K, formed by the circulation blower 14 and the duct 11, into the incubation chamber 4.

On the back face of an outer box 21 of the insulated box body 2, the machine chamber 19 is provided in which the motor as a driving means of the circulation blower 14, a gas supplying means 17 for supplying $CO_2$ gas to the incubation chamber 4, and electrical components, such as a control substrate, not illustrated, are disposed.

The gas supplying means 17 comprises a gas supply pipe 17A, an on-off valve 17B, and a filter 17C, and the tip of the gas supply pipe 17A is positioned within the gas passage K. In order to control the gas concentration in the incubation chamber 4, a jet of $CO_2$ gas supplied through the gas supply pipe 17A can be provided.

The insulated box body 2 comprises the outer box 21 made of metal, the inner box 22 made of stainless steel, an insulating material 24 provided between the outer box 21 and the inner box 22 and on the inner surfaces of the outer box 21, and an air layer (so-called an air jacket) 25 provided inside the insulating material 24. On the left and right sides, bottom face, top face, and back face of the inner box 22, forming the incubation chamber 4, heaters for heating the incubation chamber are provided as heating units (which will be described later). Heaters may also be provided on the transparent door 3 and the insulated door 7 covering the opening 2A of the incubation chamber 4.

(Configuration of Heating Units)

Figure 3:
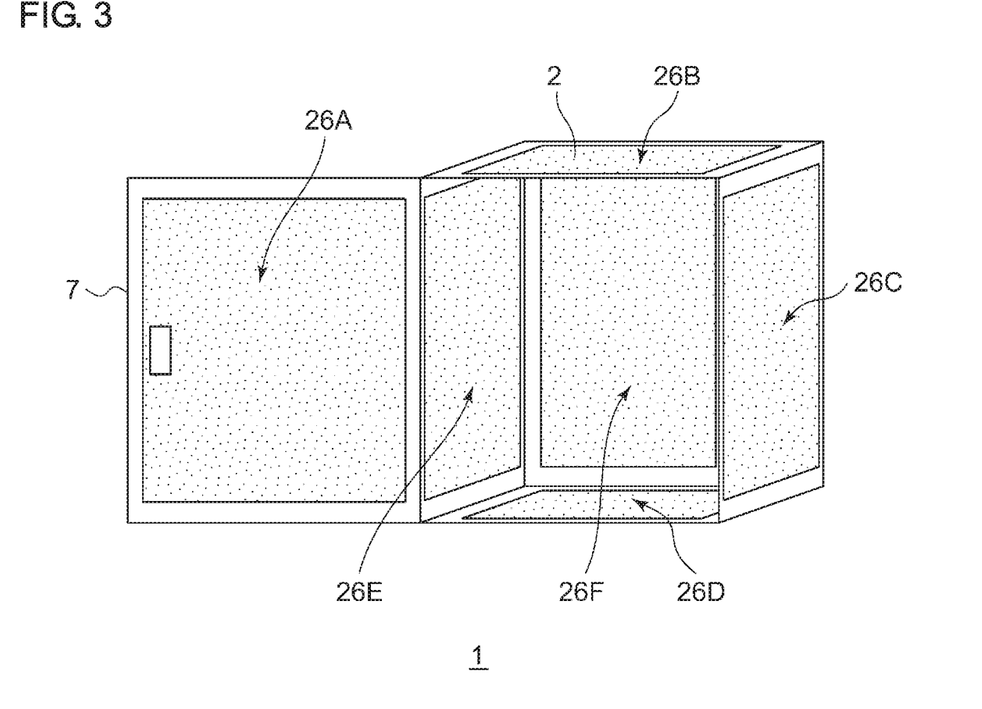
FIG. 3 is a schematic diagram for describing heating units in the incubator.

FIG. 3 is a schematic diagram for describing heating units in the incubator. Illustrations of members unnecessary for the description are appropriately omitted. The incubation chamber 4 in the aforementioned incubator 1 includes an incubation space of a rectangular parallelepiped shape surrounded by six inner faces. In the incubator 1, six heaters 26A-26F are provided as heating units for heating the respective six inner faces.

The heater 26A is pasted over the outer surface of the inner face of the insulated door 7. The heater 26B is pasted over the outer surface of the top board. The heater 26C is pasted over the outer surface of the right side. The heater 26D is pasted over the outer surface of the bottom face. The heater 26E is pasted over the outer surface of the left side. The heater 26F is pasted over the outer surface of the back face.

Figure 4:
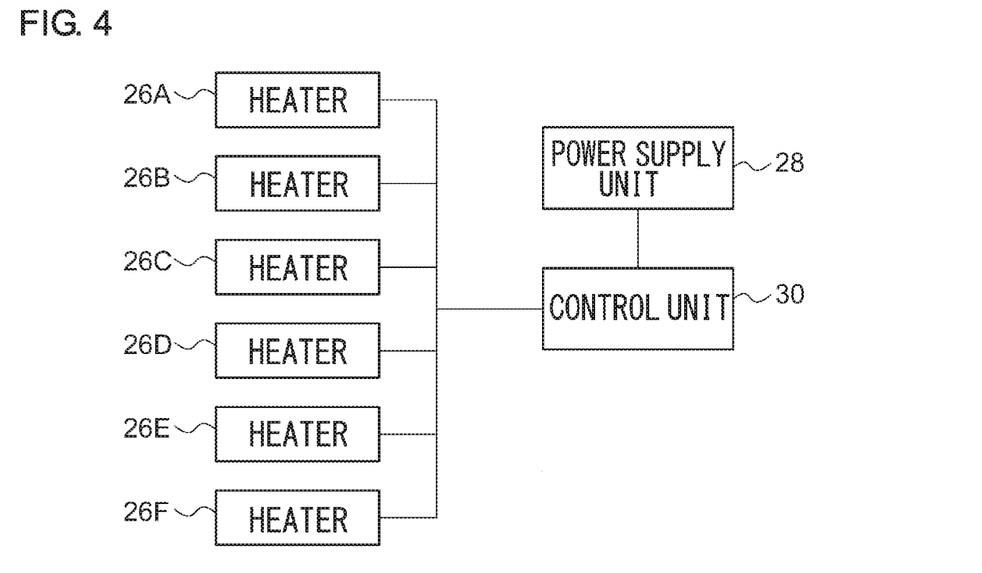
FIG. 4 is a block diagram that shows a configuration of a control unit that controls the heating units.
Figure 5:
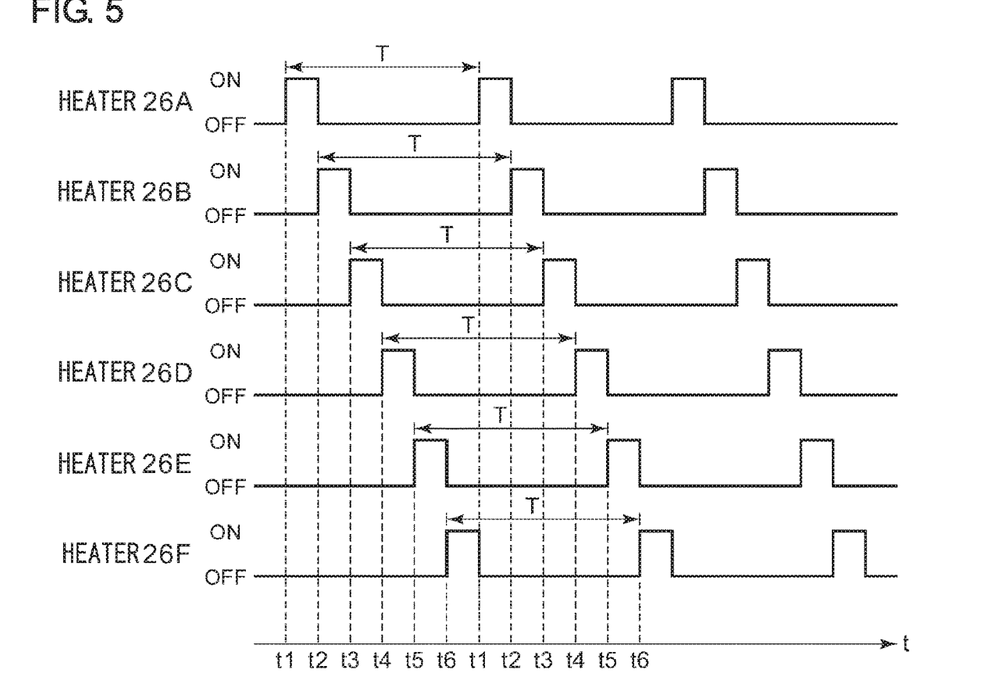
FIG. 5 is a timing chart that shows variation of the magnitude of electric power supplied to each of the heating units according to a first embodiment.

FIG. 4 is a block diagram that shows a configuration of a control unit that controls the heating units. FIG. 5 is a timing chart that shows variation of the magnitude of electric power supplied to each of the heating units according to the first embodiment.

The incubator 1 of the first embodiment comprises: the insulated box body 2 including the incubation chamber 4 as an incubation space surrounded by multiple inner faces; the humidification pan 15 as a humidifying unit that humidifies the inside of the incubation chamber 4; the heaters 26A-26F that heat the respective multiple inner faces of the incubation chamber 4 with electric power supplied; a power supply unit 28 that supplies electric power; and a control unit 30 that controls the magnitude of electric power supplied to each of the heaters.

The control unit 30 repeatedly changes the magnitude of electric power supplied to the heater 26A at timing t1 (period T), repeatedly changes the magnitude of electric power supplied to the heater 26B at timing t2 (period T), repeatedly changes the magnitude of electric power supplied to the heater 26C at timing t3 (period T), repeatedly changes the magnitude of electric power supplied to the heater 26D at timing t4 (period T), repeatedly changes the magnitude of electric power supplied to the heater 26E at timing t5 (period T), and repeatedly changes the magnitude of electric power supplied to the heater 26F at timing t6 (period T).

The timing t1-t6 is different from each other. Also, the period T of the repetitive change of electric power may not necessarily be the same for all the heaters. For example, a period T' of part of the heaters may be made different from the period T of the other heaters. Further, the period T of a heater may not necessarily be always the same. For example, after electric power is changed with a period T1, it may be changed with a period T2 (T2≠T1) and then changed with the period T1 again.

In the first embodiment, changing the magnitude of electric power means changing the state between that where electric power is not supplied (OFF) and that where a predetermined amount of electric power is supplied (ON); however, it is not limited to such changing. For example, it may be changing the state between that where a first amount (greater than zero) of electric power is supplied and that where a second amount, greater than the first amount, of electric power is supplied.

Even though each of the temperature and humidity, detected by a sensor or the like, in a region of the incubation chamber 4 stands at a value within a desired range and electric power is stably supplied to each of the heaters 26A-26F, the temperatures of the multiple inner faces forming the incubation chamber 4 are not necessarily completely uniform. Accordingly, if there is a part having a relatively low temperature in a certain region within the multiple inner faces for a long time, dew condensation may be caused in the region. In the incubator 1 according to the present embodiment, however, the state of heating by each heater can be repeatedly changed at different timing on each of the multiple inner faces of the incubation chamber 4 forming an incubation space, thereby preventing the situation where a part having a relatively low temperature continuously exists in a certain region for a long time. Consequently, dew condensation can be prevented.

Second Embodiment

Figure 6:
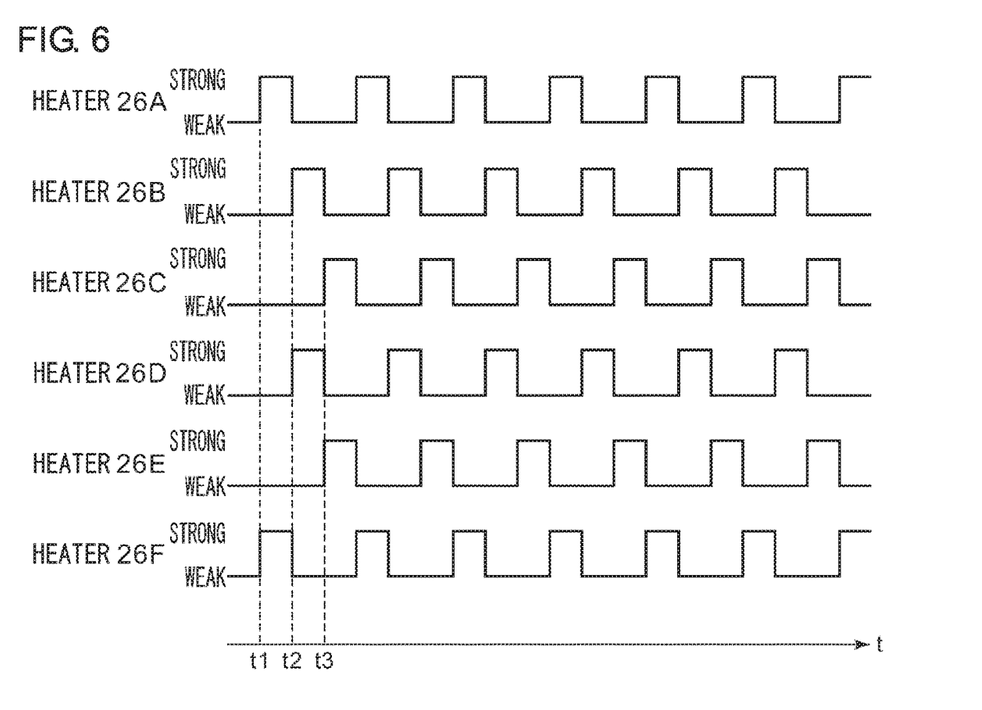
FIG. 6 is a timing chart that shows variation of the magnitude of electric power supplied to each of the heating units according to a second embodiment.

FIG. 6 is a timing chart that shows variation of the magnitude of electric power supplied to each of the heating units according to a second embodiment.

The control unit 30 according to the second embodiment repeatedly changes the magnitude of electric power supplied to the heaters 26A and 26F at timing t1 (period T), repeatedly changes the magnitude of electric power supplied to the heaters 26B and 26D at timing t2 (period T), and repeatedly changes the magnitude of electric power supplied to the heaters 26C and 26E at timing t3 (period T). When the magnitude of electric power supplied to multiple heaters is repeatedly changed at the same timing, the multiple heaters may be configured as a single heater. For example, the heaters 26B and 26D, or the heaters 26C and 26E may be configured as one heater.

Third Embodiment

Figure 7:
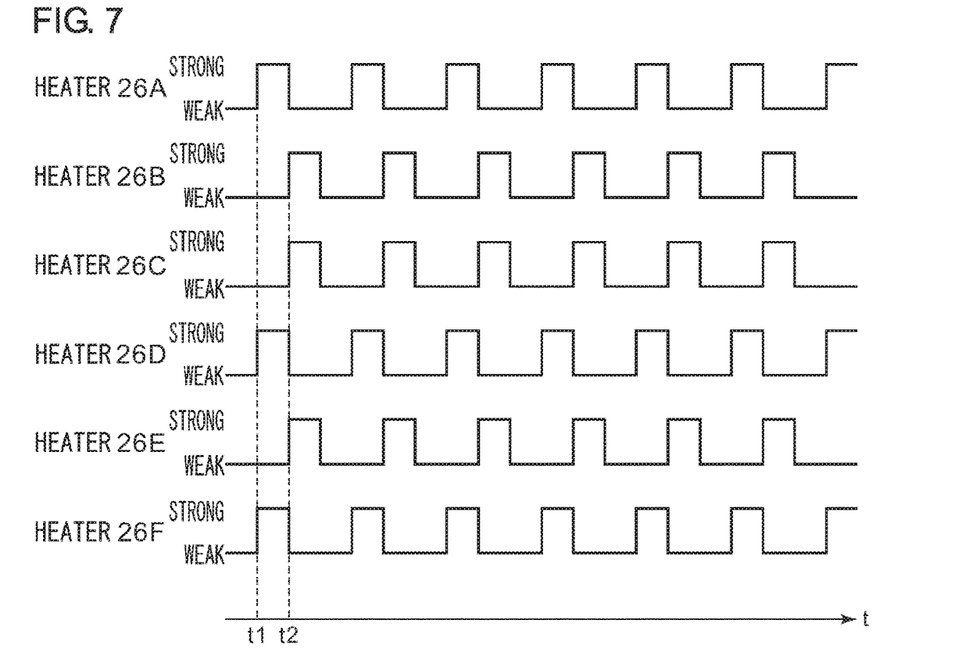
FIG. 7 is a timing chart that shows variation of the magnitude of electric power supplied to each of the heating units according to a third embodiment.

FIG. 7 is a timing chart that shows variation of the magnitude of electric power supplied to each of the heating units according to a third embodiment.

The control unit 30 according to the third embodiment repeatedly changes the magnitude of electric power supplied to the heaters 26A, 26D, and 26F at timing t1 (period T), and repeatedly changes the magnitude of electric power supplied to the heaters 26B, 26C, and 26E at timing t2 (period T). When the magnitude of electric power supplied to multiple heaters is repeatedly changed at the same timing, the multiple heaters may be configured as a single heater. For example, the heaters 26D and 26F, or the heaters 26B, 26C, and 26E may be configured as one heater.

Fourth Embodiment

Figure 8:
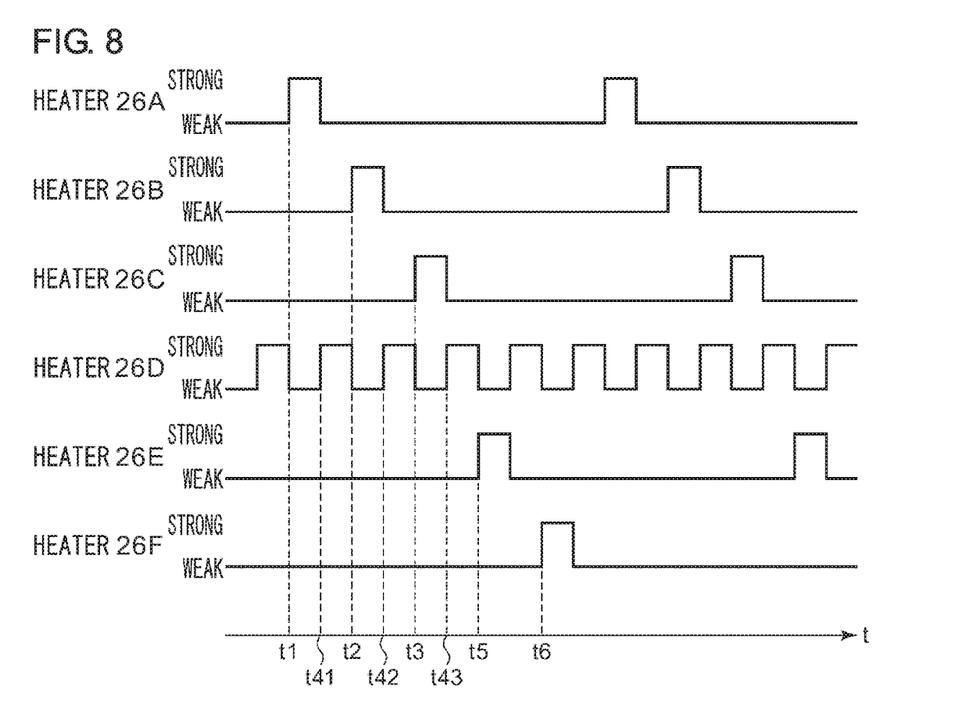
FIG. 8 is a timing chart that shows variation of the magnitude of electric power supplied to each of the heating units according to a fourth embodiment.

FIG. 8 is a timing chart that shows variation of the magnitude of electric power supplied to each of the heating units according to a fourth embodiment.

As shown in FIG. 2, the humidification pan 15 is disposed near the bottom face of the incubation chamber 4. Therefore, the control unit 30 according to the fourth embodiment repeatedly changes the magnitude of electric power supplied to the heater 26A at timing t1 (period T), repeatedly changes the magnitude of electric power supplied to the heater 26B at timing t2 (period T), repeatedly changes the magnitude of electric power supplied to the heater 26C at timing t3 (period T), repeatedly changes the magnitude of electric power supplied to the heater 26D at timing t41-t43 (period T/2), repeatedly changes the magnitude of electric power supplied to the heater 26E at timing t5 (period T), and repeatedly changes the magnitude of electric power supplied to the heater 26F at timing t6 (period T).

Namely, the control unit provides control so that electric power supplied to the heater 26D is greater than electric power supplied to each of the other heaters. This prevents dew condensation near the bottom face, where a temperature drop is more likely to occur because of heat consumption due to vaporization of water in the humidification pan 15 and a natural temperature gradient, by heating the bottom face more than the other inner faces.

Fifth Embodiment

Figure 9:
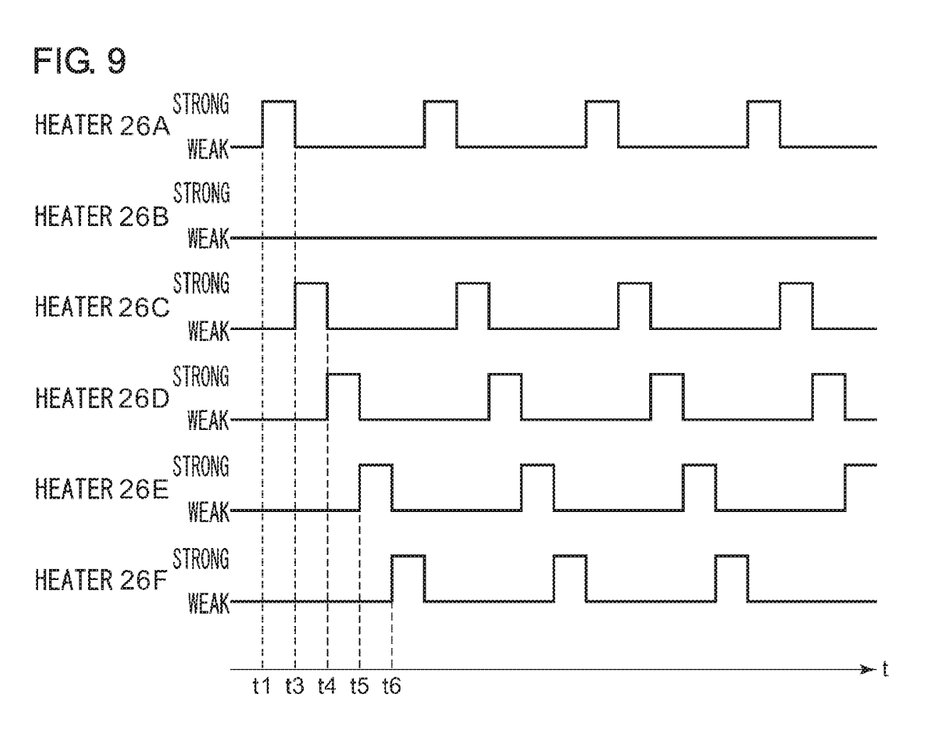
FIG. 9 is a timing chart that shows variation of the magnitude of electric power supplied to each of the heating units according to a fifth embodiment.

FIG. 9 is a timing chart that shows variation of the magnitude of electric power supplied to each of the heating units according to a fifth embodiment.

The control unit 30 according to the fifth embodiment provides control so that electric power supplied to the heater 26B is less than electric power supplied to each of the other heaters. Accordingly, heating near the top board, where the temperature tends to rise, can be restrained, so that the temperatures within the incubation space can be made more uniform.

The incubator set forth above can also be expressed as follows. Namely, the incubator 1 comprises: the insulated box body 2 including the incubation chamber 4 surrounded by multiple inner faces; the humidification pan 15 that humidifies the incubation chamber 4; the multiple heaters 26A-26F that heat the multiple inner faces; and the control unit 30 that controls the magnitude of electric power supplied to each of the multiple heaters 26A-26F. The control unit 30 controls electric power supplied to each of the multiple heaters 26A-26F so as to repeatedly change the temperature distribution on the multiple inner faces at predetermined timing.

Namely, the incubator 1 according to each of the aforementioned embodiments repeatedly changes the temperature distribution on the multiple inner faces forming the incubation chamber 4 at predetermined timing, thereby preventing the situation where a part having a relatively low temperature continuously exists in a certain region for a long time. Consequently, dew condensation can be prevented.

The incubator 1 may be an incubator connected to another device, such as an isolator, or may be configured as a system including an isolator. Although the incubator 1 includes the heaters 26A-26F for heating the respective six inner faces surrounding the incubation space as heating units controlled to be repeatedly changed at predetermined timing, the number and the arrangement of the heaters are not limited to those described in the embodiments. The number of the heaters may be at least two, and, with regard to the arrangement of the heaters, the six faces may not necessarily be sectioned for each inner face; for example, the inner box 22 may be sectioned vertically or horizontally, and two heaters for heating the respective sectioned regions may be provided. Also, the inner box 22 may be sectioned into regions that include the respective corners. In this way, the multiple inner faces surrounding the incubation space may be sectioned into at least two regions, and the heating units controlled to be repeatedly changed at predetermined timing may be provided to heat the respective regions.

The present invention has been described with reference to each of the aforementioned embodiments. However, the present invention is not limited thereto and also includes a form resulting from appropriate combination or replacement of the configurations in the embodiments. It is also to be understood that appropriate changes of the combination or the order of processes in the embodiments or various modifications, including design modifications, may be made based on the knowledge of those skilled in the art and that such changes and modifications also fall within the scope of the present invention.

The invention claimed is:

1. A method of controlling an incubator, the method comprising:
   humidifying an incubation space of the incubator;
   heating inner surfaces surrounding the incubation space with electric power supplied to heaters, respectively, the heaters being provided to heat the inner surfaces, respectively; and
   periodically and repeatedly changing a magnitude of the electric power supplied to each of the heaters at predetermined timing different from each other.

2. The method according to claim 1, wherein
   the magnitude of the electric power supplied to each of the heaters is changed between a first magnitude and a second magnitude; and
   the first magnitude is to provide first electric power to each heater, and the second magnitude is to provide second electric power that is greater than that of the first electric power, both the first electric power and the second electric power maintaining each heater to turn on.

3. The method according to claim 2, wherein a period during which one of the first and second magnitudes are maintained is variable.

4. The method according to claim 3, wherein the period for one of the heaters is different from that of another one of the heaters.

5. A method of controlling an incubator, the method comprising:
   humidifying an incubation space of the incubator;
   supplying electric power to heaters to heat inner surfaces surrounding the incubation space; and
   controlling a magnitude of electric power supplied to each heater to repeatedly change a temperature distribution within the incubation space, wherein
   the controlling includes at least first to third temperature distribution patterns to control the heaters, and controls the heaters to periodically change the temperature distribution based on the at least first to third temperature distribution patterns.

* * * * *